US008580491B2

(12) United States Patent
Ahn et al.

(10) Patent No.: US 8,580,491 B2
(45) Date of Patent: Nov. 12, 2013

(54) CANCER DIAGNOSIS MARKER USING THE ABERRANT GLYCOSYLATION OF A PROTEIN

(75) Inventors: Yeong Hee Ahn, Chungcheongbuk-do (KR); Jong Shin Yoo, Seoul (KR)

(73) Assignee: Korea Basic Science Institute, Daejeon (KR)

( * ) Notice: Subject to any disclaimer, the term of this patent is extended or adjusted under 35 U.S.C. 154(b) by 0 days.

(21) Appl. No.: 13/375,545

(22) PCT Filed: Dec. 24, 2010

(86) PCT No.: PCT/KR2010/009323
§ 371 (c)(1),
(2), (4) Date: Dec. 1, 2011

(87) PCT Pub. No.: WO2011/081369
PCT Pub. Date: Jul. 7, 2011

(65) Prior Publication Data
US 2012/0258484 A1  Oct. 11, 2012

(30) Foreign Application Priority Data
Dec. 29, 2009 (KR) ........................ 10-2009-0133088

(51) Int. Cl.
*C12Q 1/00* (2006.01)
*G01N 33/53* (2006.01)
*G01N 33/48* (2006.01)
*G01N 33/00* (2006.01)

(52) U.S. Cl.
USPC .................... 435/4; 435/7.1; 436/64; 436/86; 436/87

(58) Field of Classification Search
None
See application file for complete search history.

(56) References Cited

U.S. PATENT DOCUMENTS

| 4,146,603 | A | 3/1979 | Davidson et al. |
| 6,828,424 | B2 | 12/2004 | Greene et al. |
| 7,807,392 | B1 | 10/2010 | Domon et al. |
| 2009/0208926 | A1 | 8/2009 | Block et al. |
| 2012/0258471 | A1 | 10/2012 | Ahn et al. |

FOREIGN PATENT DOCUMENTS

| KR | 10-0846354 B1 | 7/2008 |
| KR | 10-2010-0120788 | 11/2010 |
| WO | WO 2009/048196 | 4/2009 |

OTHER PUBLICATIONS

Kim et al., Identification of target proteins of N-acetylglucosaminyl transferase V in human colon cancer and implications of protein tyrosine phosphatase kappa in enhanced cancer cell migration, Proteomics, 2006, 6, 1187-1191.*
Pierce (Antibody Purification Methods, Retrieved from the Internet <URL: http://www.piercenet.com/browse.cfm?fldID=4E032172-5056-8A76-4EAE-8D395D2DCDA3>, Retrieved on Apr. 18, 2013).*
Cui et al. (Computational prediction of human proteins that can be secreted into the bloodstream, Bioinformatics, vol. 24, No. 20, 2008, pp. 2370-2375).*
International Search Report prepared by the Korean Intellectual Propert Office for International Application No. PCT/KR2010/008666, dated Aug. 11, 2011.
Yang et al. "Multilectin Affinity Chromatography fro Characterization of Multiple Glycoprotein Biomarker Candidates in Serum from Breast Cancer Patients." *Clinical Chemistry* 52:10, 1897-1905 (2006).
Geng et al. "Proteomics of glycoproteins based on affinity selection of glycopeptides from tryptic digests." *Journal of Chromatography B.* Biomed Sci Appl. Mar. 2001 10:752(2):293-306.
International Search Report prepared by the Korean Intellectual Property Office on Sep. 28, 2011, for International Application No. PCT/KR2010/009323.
Ahn et al., "Quantitative Analysis of an Aberrant Glycoform of TIMP1 from Colon Cancer Serum by L-PHA-Enrichment and SISCAPA with MRM Mass Spectrometry," J. Proteome Res., 2009, vol. 8, pp. 4216-4224.
Greene et al., Dec. 17, 2004, GenBank Accession No. AAW19207, 1 page.
Otsuki et al., Jul. 3, 2008, GenBankAccession No. BAG52016, 1 page.
Otsuki et al., "Signal Sequence and Keyword Trap in silico for Selection of Full-Length Human cDNAs Encoding Secretion or Membrane Proteins from Oligo-Capped cDNA Libraries," DNA Res., 2005, vol. 12, pp. 117-126.

* cited by examiner

*Primary Examiner* — Suzanne M Noakes
*Assistant Examiner* — Jae W Lee
(74) *Attorney, Agent, or Firm* — Sheridan Ross P.C.

(57) ABSTRACT

The present invention relates to a method for diagnosing cancer using information on the aberrant glycosylation of a glycoprotein. More precisely, the present invention relates to a cancer diagnosis peptide marker, which is screened by: a step of separating, using a lectin, a glycoprotein which is aberrantly glycosylated in accordance with the occurrence of cancer; and a step of selecting a hydrolyzed peptide marker derived from the aberrantly glycosylated glycoprotein by observing the quantitative changes in the separated glycoprotein. The present invention also relates to a method for diagnosing cancer using the peptide marker as an agent.

5 Claims, 5 Drawing Sheets

SEQUENCE LISTING

<160> NUMBER OF SEQ ID NOS: 6

<210> SEQ ID NO 1
<211> LENGTH: 20
<212> TYPE: PRT
<213> ORGANISM: Homo sapiens

<400> SEQUENCE: 1

Glu Pro Leu Asp Pro Asn Gly Ile Ile Thr Gln Tyr Glu Ile Ser Tyr
1               5                   10                  15

Ser Ser Ile Arg
            20

<210> SEQ ID NO 2
<211> LENGTH: 18
<212> TYPE: PRT
<213> ORGANISM: Homo sapiens

<400> SEQUENCE: 2

Gly Ala Pro Ile Ser Ala Tyr Gln Ile Val Val Glu Glu Leu His Pro
1               5                   10                  15

His Arg

<210> SEQ ID NO 3
<211> LENGTH: 13
<212> TYPE: PRT
<213> ORGANISM: Homo sapiens

<400> SEQUENCE: 3

Leu Trp His Leu Asp Pro Asp Thr Glu Tyr Glu Ile Arg
1               5                   10

<210> SEQ ID NO 4
<211> LENGTH: 13
<212> TYPE: PRT
<213> ORGANISM: Homo sapiens

<400> SEQUENCE: 4

Gly Ser Gly Val Ser Asn Phe Ala Gln Leu Ile Val Arg
1               5                   10

<210> SEQ ID NO 5
<211> LENGTH: 12
<212> TYPE: PRT
<213> ORGANISM: Homo sapiens

<400> SEQUENCE: 5

Gly Leu Asn Pro Gly Thr Leu Asn Ile Leu Val Arg
1               5                   10

<210> SEQ ID NO 6
<211> LENGTH: 10
<212> TYPE: PRT
<213> ORGANISM: Homo sapiens

<400> SEQUENCE: 6

Ser Leu Gln Gly Thr Ser Phe Glu Asn Lys
1               5                   10

CANCER DIAGNOSIS MARKER USING THE ABERRANT GLYCOSYLATION OF A PROTEIN

CROSS REFERENCE TO RELATED APPLICATIONS

This application is a national stage application under 35 U.S.C. 371 of PCT Application No. PCT/KR2010/009323 having an international filing date of 24 Dec. 2010, which designated the United States, which PCT application claimed the benefit of Korean Application No. 10-2009-0133088 filed 29 Dec. 2009, the entire disclosure of each of which is incorporated herein by reference.

BACKGROUND OF THE INVENTION

1. Field of the Invention

The present invention relates to a method for diagnosing cancer by quantitative analysis of a glycoprotein which is aberrantly glycosylated in accordance with the occurrence of cancer.

2. Description of the Related Art

Proteins are involved in various life-supporting activities and post-translationally modified by signal transmission whenever necessary. The most representative post-translational modification processes are glycosylation and phosphorylation. In particular, regarding glycosylation of a glycoprotein, many monosaccharides existing on the surface of cell membrane are passed through the cell membrane by signal transduction, leading to glycosylation of a required protein by N-acetylglucosaminyltransferase. Such glycoprotein plays an important role as being located on the outer membrane. Once glycoproteins finish their required role, they proceed to glucolysis by glycosidase. However, many glycoproteins or glycolipids located on the surface of cell membrane often experience aberrant glycosylation by the specific signal such as oncogene, etc. Many diseases have been known to be closely related to such abnormal functions of glycosidase and glycosyltransferase triggered by abnormal signal transduction by oncogene (Kim, Y. J., et al., *Glycoconj. J.,* 1997, 14, 569-576., Hakomori, S., *Adv. Cancer Res.,* 1989, 52, 257-331., Hakomori, S., *Cancer Res.,* 1996, 56, 5309-5318).

In the aberrant glycosylation pattern observed in cancer cells, changes in the size of N-linked glycosylation, the number of side chains, and the increase of sialylation and fucosylation are observed along with the changes in the size of glycan chain by polylactosamine formation. Such glycoprotein, thus, can be used as a cancer marker for the identification of cancer and confirmation of cancer progression by taking advantage of the said pattern observed in the aberrant glycosylation. Such aberrant glycosylation affects functions of the glycosylated protein such as folding, recognition, and solubility, etc by the specificity of the structure and the size of glycan chain (Varki, A. et al., *Glycobiology* 1993, 3, 97-130., Parodi, A. J. et al., *Annu. Rev. Biochem.* 2000, 69, 69-93). In particular, such glycotransferase as N-acetylglucosaminyltransferase that is abnormally activated in cancer cells induces the aberrant glycosylation which facilitates the distinguishment of cancer cells from normal cells, suggesting that the aberrantly glycosylated glycoprotein can be used as a marker for cancer diagnosis (Dennis, J. W.; Laferte, S.; Waghorne, C.; Breitman, M. L.; Kerbel, R. S. Beta 1-6 branching of Asn-linked oligosaccharides is directly associated with metastasis. *Science* 1987, 236: 582-585). The glycoprotein harboring information on cancer is secreted to extracellular media once it completes its role therein, or is fallen off the cell membrane and shed to media. Therefore, diverse culturing media for cancer cells, cancer tissue lysis, and patient's blood samples can be proper materials for detection of the glycoprotein containing information on cancer, which can be used as a marker for cancer diagnosis.

Difference of glycosylation in protein samples obtained from the normal group and the cancer patient group can be an important clue to distinguish patient group from normal group. Up to date, many analysis methods have been reported to tell the difference of a glycoprotein. Glycan profiling is an example of the methods to screen difference in glycosylation of a protein, which analyzes glycans obtained from hydrolysis of glycoproteins by using mass spectrometer (Barkauskas. et al., *Bioinformatics,* 2009, 25, 251-257). However, this method has a disadvantage of losing information on the glycosylated isoform in relation to characteristics of glycosylation and glycosylated structure in the specific glycosylation site of each protein because this method only enables mass analysis of numbers of glycosylated isoform mixtures composed of all different isoforms originated from different proteins and glycosylation sites but having equal weights.

Glyco-capturing method using hydrazide has been used for the enrichment of a glycoprotein (Zhang H. et al., *Nat. Biotechnol.,* 2003, 21, 660–666). However, this method has a disadvantage of losing information on specific structured aberrant glycosylation derived from cancer cells because normal glycosylation structure cannot be maintained during glycan-capturing.

To separate and enrich a glycoprotein or a glycopeptide alone, considering different structures of glycan chain, ConA (Concanavalin A), WGA (Wheat germ agglutinin), Jacalin, SNA (*Sambucus nigra* agglutinin), AAL (*Aleuria aurantia* lectin), L-PHA (Phytohemagglutinin-L), PNA (Peanut agglutinin), LCA (*Lens culimaris* agglutinin-A), ABA (*Agaricus biflorus* agglutinin), DBA (*Dolichos biflorus* agglutinin), DSA (*Datura stramonium* agglutinin), ECA (*Erythrina cristagalli* agglutinin), SBA (Soybean agglutinin), SSA (*Sambucus sieboldiana* agglutinin), UEA (*Ulex europaeus* agglutinin), VVL (*Vicia villosa* lectin), BPL (*Bauhinia purpurea* lectin), or multilectin prepared by combinations of the above lectins can be used (Yang, Z. et al., *J. Chromatogr, A,* 2004, 1053, 79-88., Wang, Y. et al., *Glycobiology,* 2006, 16, 514-523). This is the method to utilize the selectivity of lectin to glycan chain structure of a glycoprotein, so that selective separation and enrichment of a glycoprotein having specific glycan chain structure can be possible. In particular, complexity of the target sample can be significantly reduced by eliminating such proteins that do not show affinity to lectin through the separation process of glycoproteins selective to lectin. The separated and enriched glycoproteins can be analyzed qualitatively and quantitatively by using various analysis methods.

One of those methods for analyzing a glycoprotein by using the selectivity of lectin to glycan chain structure of a glycoprotein is lectin-blotting. This method is generally performed along with immunoblotting characterized by high selectivity against certain proteins. At this time, an antibody against the antigen protein is required. If the corresponding antibody is not prepared, the protein cannot be analyzed by this method. Lectin-blotting utilizes gel-separation technique, suggesting that there is still a disadvantage of limited analyzing speed and questions remain on liability in quantitative analysis. When array technique using an antibody and lectin is used, analyzing speed and sensitivity can be significantly improved, compared with the conventional lectin-blotting (Forrester, S. et. al., Low-volume, high-throughput sandwich immunoassays for profiling plasma proteins in mice:

identification of early-stage systemic inflammation in a mouse model of intestinal cancer. *Mol Oncol* 2007, 1(2): 216-225). However, this technique requires a liable antibody and it is very difficult to obtain each antibody against every glycoprotein newly identified at a massive scale.

In the meantime, mass spectrometry is a very useful method for high-speed, high-sensitivity qualitative and quantitative analysis of very complicated proteome samples. In particular, multiple reaction monitoring is the method to analyze quantitatively, with high liability, polypeptides having comparatively small molecular weights which are usually generated by hydrolysis of a protein. This method is especially useful when an antibody against the target protein cannot be obtained (Kuhn, E. et. al., Quantification of C-reactive protein in the serum of patients with rheumatoid arthritis using multiple reaction monitoring mass spectrometry and $^{13}$C-labeled peptide standards. *Proteomics* 2004, 4(4): 1175-1186). MRM is an analysis method with high sensitivity that facilitates selective analysis of the target peptide from very complicated samples by at least one of liquid chromatography and two times of precursor mass selection and fragment ion selection from those peptides generated by hydrolysis of the target protein (Anderson L, et al., *Mol. Cell Proteomics*. 2006, 5, 573-588).

The sample like plasma proteome is composed of at least 50,000 constituents and the density of protein components is very dynamic (1~$10^{12}$, pg/ml). So, a biomarker candidate protein existing at a very low concentration is hard to detect and analyze quantitatively by liquid chromatography-mass spectrometry (LC/MS/MS) (Anderson N. L. et al., *Mol. Cell Proteomics*. 2002, 1, 845-867). To minimize complexity of the sample for efficient detection of a disease biomarker in plasma, proteins taking about 90% or more of plasma proteome such as albumin, IgG, IgA, transferrin and haptoglobin are first eliminated. And then the resultant proteome is used for analysis. Even after the minimization of the complexity of the sample by eliminating those proteins exiting at high concentrations in plasma and the increased high selectivity against the target peptide by LC-MRM, if a target marker protein exists at a very low concentration in the sample, the concentration of the marker protein or the hydrolyzed marker peptide is increased through enrichment process of the marker protein or the marker peptide by using immunoaffinity to improve LOD (limit of detection) and LOQ (limit of qualification).

The present inventors tried to develop a method for diagnosing cancer by using quantitative information on a glycoprotein which is aberrantly glycosylated in accordance with the occurrence of cancer, during which the inventors obtained polypeptides by hydrolyzing the said glycoprotein after separating and concentrating the glycoprotein, selected hydrolyzed marker peptides derived from the marker glycoprotein characteristically demonstrating cancer specific glycosylation, and finally completed this invention by confirming that the said marker peptides could be effectively used for cancer diagnosis.

SUMMARY OF THE INVENTION

It is an object of the present invention to provide a method for diagnosing cancer using specific polypeptides that can tract quantitative changes in glycoproteins glycosylated in a specific manner by the occurrence of cancer.

It is another object of the present invention to provide a kit for diagnosing cancer containing the said polypeptide specific antibody.

To achieve the above objects, the present invention provides a method to provide information for cancer diagnosis comprising the following steps:

1) separating and concentrating glycoproteins by treating a sample obtained from a subject with lectin;
2) hydrolyzing the glycoproteins of step 1) to obtain polypeptides;
3) quantitatively analyzing the polypeptides of step 2); and
4) diagnosing cancer or high risk of cancer when the subject has at least one of those polypeptides selected from the group consisting of those polypeptides having the molecular weights of 2294.1, 2015.0, 1685.8, 1346.7, 1265.7 and 1109.5 confirmed by the quantitative analysis of step 3).

The present invention also provides a method to provide information for cancer diagnosis comprising the following steps:

1) separating and concentrating glycoproteins by treating a sample obtained from a subject with lectin;
2) hydrolyzing the glycoproteins of step 1) to obtain polypeptides;
3) sequencing and quantitatively analyzing the polypeptides of step 2); and
4) diagnosing cancer or high risk of cancer when the subject has at least one of those polypeptides selected from the group consisting of those polypeptides having the amino acid sequences represented by SEQ. ID. NO: 1-NO: 6 confirmed by the sequencing and quantitative analysis of step 3).

The present invention also provides a kit for diagnosing cancer containing an antibody or a combination of antibodies specifically binding to the polypeptide having one of the amino acid sequences each represented by SEQ. ID. NO: 1-NO: 6.

The present invention also provides a biochip for diagnosing cancer on which a biomolecule specifically binding to the polypeptide having one of the amino acid sequences each represented by SEQ. ID. NO: 1-NO: 6 is integrated on the solid substrate.

The present invention also provides a use of the antibody or the combination of antibodies specifically binding to the polypeptide having one of the amino acid sequences each represented by SEQ. ID. NO: 1-NO: 6 for the preparation of a kit for diagnosing cancer.

In addition, the present invention provides a use of the biomolecule specifically binding to the polypeptide having one of the amino acid sequences each represented by SEQ. ID. NO: 1-NO: 6 for the preparation of a biochip for diagnosing cancer.

Advantageous Effect

The present invention provides a method to distinguish effectively the cancer patient group from the normal healthy group by performing quantitative analysis of the marker glycoprotein isoform having a cancer specific glycan chain structure that is quantitatively changed sensitively by N-acetylglucosaminyltransferase, the glycosyltransferase overexpressed in many types of cancer cells. The method of the present invention facilitates fast and simple diagnosis of cancer from the sample of a subject by performing quantitative analysis of the hydrolyzed marker peptide containing the information on the amount of the marker glycoprotein isoform having a cancer specific glycan chain structure. At this time, the selected peptide can be effectively used as a marker for cancer diagnosis.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
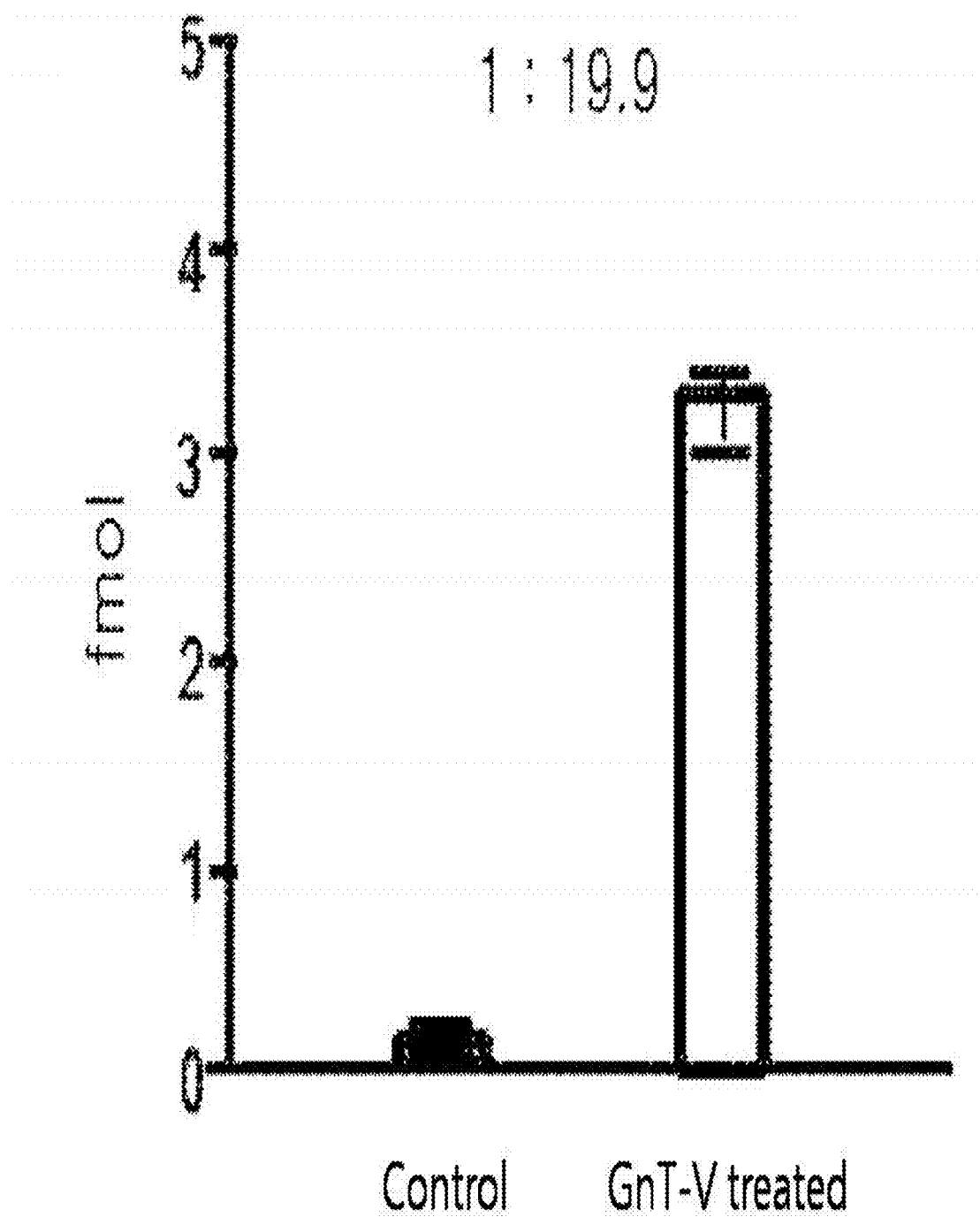
FIG. 1 is a diagram illustrating the quantitative analysis result of the marker glycoprotein having a cancer specific glycan chain structure by using the marker peptide representative after performing lectin-separation with both GnT-V overexpressing group (GnT-V treated) and normal control group. In the GnT-V treated group, the expression of the marker glycoprotein having a cancer specific structure was significantly increased (approximately 19.9 fold higher), proving high specificity.

Hereinafter, the present invention is described in detail.

The present invention provides a method for diagnosing cancer using information on specific glycosylation of a glycoprotein.

Particularly, the present invention provides a method for diagnosing cancer by using one or more peptide markers selected by the following steps: separating glycoproteins containing specific glycan chain related to cancer development from a sample by using lectin; hydrolyzing the separated glycoproteins to give peptides; and selecting marker peptides among the peptide samples obtained by hydrolysis above that can track quantitative changes in glycoproteins glycosylated in a specific manner by the occurrence of cancer.

In a preferred embodiment of the present invention, it is preferred to diagnose cancer by the method comprising the following steps, but not always limited thereto:

1) separating and concentrating glycoproteins by treating a sample obtained from a subject with lectin;
2) hydrolyzing the glycoproteins of step 1) to obtain polypeptides;
3) quantitatively analyzing the polypeptides of step 2); and
4) diagnosing cancer or high risk of cancer when the subject has at least one of those polypeptides selected from the group consisting of those polypeptides having the molecular weights of 2294.1, 2015.0, 1685.8, 1346.7, 1265.7 and 1109.5 confirmed by the quantitative analysis of step 3).

In another preferred embodiment of the present invention, it is preferred to diagnose cancer by the method comprising the following steps, but not always limited thereto:

1) separating and concentrating glycoproteins by treating a sample obtained from a subject with lectin;
2) hydrolyzing the glycoproteins of step 1) to obtain polypeptides;
3) sequencing and quantitatively analyzing the polypeptides of step 2); and
4) diagnosing cancer or high risk of cancer when the subject has at least one of those polypeptides selected from the group consisting of those polypeptides having the amino acid sequences represented by SEQ. ID. NO: 1-NO: 6 confirmed by the sequencing and quantitative analysis of step 3).

In this invention, the sample is the one that can be obtained from living things harboring proteins containing information related to cancer development and progress, which is exemplified by biological tissue, cell line or culture fluid originated from culture of the biological tissue, saliva, and blood. Particularly, the glycoprotein harboring information on cancer is secreted to extracellular media once it finishes playing its role, or is fallen off the cell membrane and shed to media. Therefore, culturing media of various cancer cell lines and patients' blood samples are good samples for the screening of glycoproteins containing information on cancer, which are cancer markers. In the case of blood sample, difference of concentrations of each protein component existing in blood is very huge. So, pre-treatment is preferred to minimize the complexity of a sample by using protein removal column (ex, MARS, Multiple Affinity Removal System), but not always limited thereto.

In this invention, 'cancer specific glycosylation of a glycoprotein' means that glycosylation of a protein is induced abnormally in cancer patients and those having history of cancer. Such specific glycosylation can occur at specific glycan chain sites connected to glycosylation sites such as asparagine, threonin, or serine site. The glycan chain having a cancer specific structure shows glycan microheterogeneity by sharing one glycosylation site with the glycan chain with normal structure. Thus, the said specific glycan chain exists among many glycan-isoforms in one glycosylation site at a very low concentration, nonstoichiometrically to the protein. Therefore, to measure the quantitative changes of such specific glycan chain accurately, it is preferred to separate and concentrate the specific glycan chain from various glycan-isoforms, but not always limited thereto.

In this invention, lectin can be used to separate and concentrate the isoform having specific glycan chain from many glycan-isoforms having different glycan chain structures. This is the method to take advantage of selectivity of lectin against glycan chain structure of a glycoprotein, so that it facilitates selective separation and concentration of marker glycoproteins having a specific glycan chain structure. According to the glycan chain structure, a variety of lectins such as ConA, WGA, Jacalin, SNA, AAL, L-PHA, PNA, LCA, ABA, DBA, DSA, ECA, SBA, SSA, UEA, VVL, or BPL can be used either alone or together as a combination for the separation and concentration. Various lectins can be used for the separation of proteins having different glycan-isoforms selectively from the total samples.

In a preferred embodiment of the present invention, the glyco-isoform having glycan chain with specific structure was separated and concentrated by using L-PHA to trace the changes of specific glycosylation (increase of side chain of glycan chain by the connection of β-1,6-GlcNAc) mediated by N-acetylglucosaminyltransferase, the glycosyltransferase overexpressed in many types of cancer cells. At this time, many proteins not showing affinity to L-PHA were eliminated during the separation procedure of L-PHA selective glycoproteins, suggesting that the complexity of a target sample was significantly decreased.

In this invention, it is preferred to hydrolyze the high molecular weight proteins separated by using lectin into peptide fragments having smaller molecular weight to increase efficiency of analysis. To obtain peptides by hydrolyzing glycoproteins, a biological method using various hydrolases or a chemical method using a chemical reagent inducing hydrolysis in a specific amino acid site can be used. At this time, one or more hydrolases selected from the group consisting of Arg-C, Asp-N, Glu-C, Lys-C, chymotrypsin and trypsin can be used, and trypsin is more preferred, but not always limited thereto. To enhance hydrolysis efficiency and efficiency in analysis of generated peptides, pre-treatment of samples such as denaturatiion, reduction, and cystein alkylation can be performed before hydrolysis.

In this invention, target peptides (marker peptides) that can track quantitative changes in marker glycoproteins glycosylated in a specific manner by the occurrence of cancer can be selected by comparative quantitative analysis of the hydrolyzed peptide samples obtained from normal and patient groups. In particular, culturing media of diverse cancer cell lines and patient's blood samples are good samples for the screening of the cancer marker that is the glycoprotein containing information on cancer. Herein, the said cancer includes every kind of cancer inducing cancer specific glycosylation, which is exemplified by colon cancer, liver cancer, stomach cancer, lung cancer, uterine cancer, breast cancer, prostatic cancer, thyroid cancer, and pancreatic cancer, etc.

In a preferred embodiment of the present invention, marker glycoprotein candidates showing quantitative changes by certain glycosylation specifically induced by N-acetylglucosaminyltransferase, the glycosyltransferase overexpressed in many types of cancer cells, were selected. Then, quantitative mass spectrometry was performed with the candidate marker peptides. Finally, the method for diagnosing cancer with the selected peptide marker was completed by confirming the cancer marker peptides affected by N-acetylglucosaminyltransferase, the glycosyltransferase overexpressed in human colon cancer cells (see Table 1).

In this invention, the marker peptides selected from the peptide samples obtained by hydrolysis after concentration using lectin can be composed of one or more peptides originated from a single glycoprotein, or can include peptides originated from different glycoproteins. Therefore, the selected marker peptides can be used for sample analysis together with at least two peptides if necessary.

To analyze the hydrolyzed peptides including marker peptides quantitatively, immune-precipitation or immuno-blotting using a peptide-specific antibody can be used along with mass spectrometry in this invention. In particular, mass spectrometry has no limitation in peptides. This method has another advantage of high speed/high sensitivity. Quantitative analysis method performed by labeling peptides with an isotope-labeled marker (iTRAQ, ICAT etc.) or multiple reaction monitoring (MRM) performed by adding stable isotope standard to the sample as an internal standard can be used. In a preferred embodiment of the present invention, MRM was performed by adding an isotope-labeled marker peptide standard to the sample as an internal standard to quantitatively analyze cancer marker peptides affected by N-acetylglucosaminyltransferase, the glycosyltransferase overexpressed in cancer cells.

Figure 2:
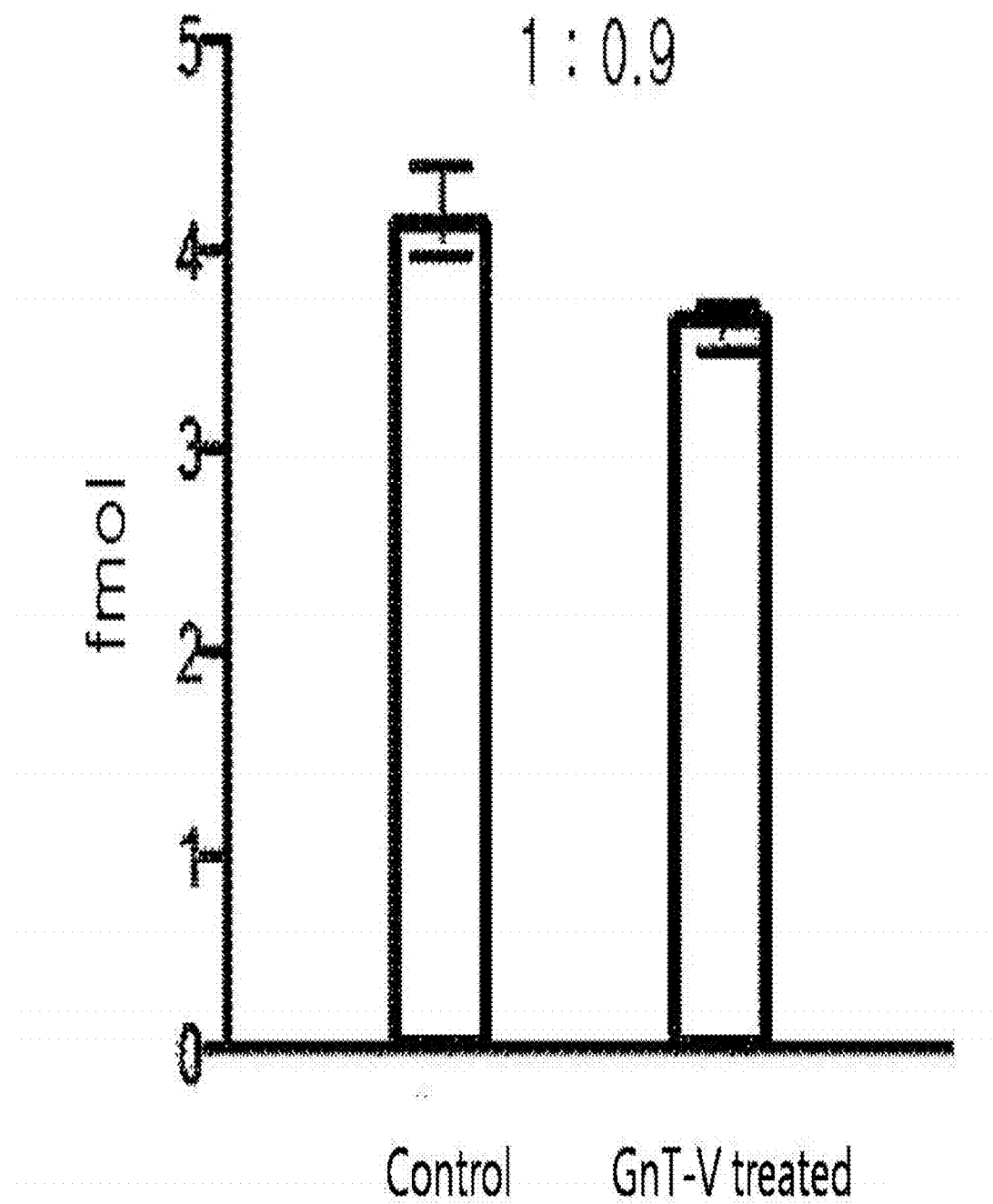
FIG. 2 is a diagram illustrating the quantitative analysis result of the total marker glycoprotein expressed in the GnT-V overexpressing group (GnT-V treated) and the normal control group by using the marker peptide representative without lectin-separation. The marker protein was a little down-regulated in the GnT-V treated group compared with when lectin separation was performed.
Figure 3:
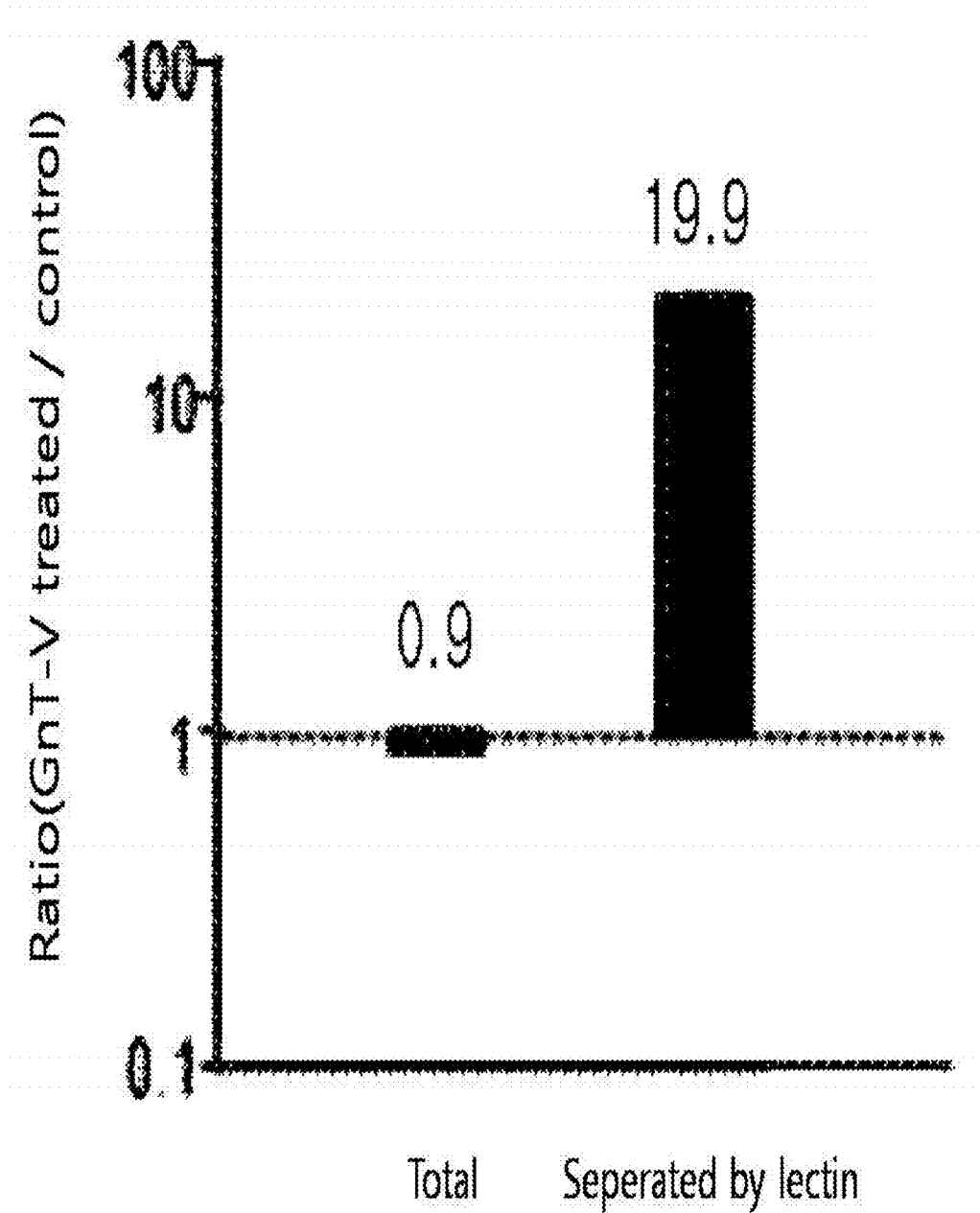
FIG. 3 is a diagram illustrating the effect of lectin separation, which favors quantification of the marker glycoprotein having aberrant glycan chain. Aberrant glycosylation was induced by the over-expression of GnT-V. The marker glycoprotein isoform separated and concentrated by lectin was significantly increased (19.9 fold), but the total marker glycoprotein in the sample was slightly decreased by the over-expression of GnT-V.

In a preferred embodiment of the present invention, the marker peptide having the peptide mass of 1685.8 was selected among the marker peptides (see Table 1) to investigate the effect of N-acetylglucosaminyltransferase V (GnT-V), the glycosyltransferase overexpressed in many types of cancer cells, on specific glycosylation of a marker glycoprotein (see FIG. 1 and FIG. 2). Glycan-isoforms having a specific glycan chain structure were separated by using lectin from the GnT-V overexpressing cell line (GnT-V-treated), and from the GnT-V not-overexpressing cell line (control), followed by MRM via hydrolysis. As a result, as shown in FIG. 1, the generation of glycan-isoform having a specific glycan-chain structure with high affinity selectively to L-PHA was remarkably increased in the sample where GnT-V was over-expressed. To confirm that the above result was attributed to the generation of glycan-isoform having a specific glycan-chain structure, the same sample was hydrolyzed without using lectin, followed by MRM using the same marker peptide. In this case, that is in the case that separation process of glycan-isoform having a specific glycan-chain structure by using lectin is skipped, the amount of the measured marker peptide represents total amount of the marker glycoprotein including all of glycan-isoforms in the GnT-V overexpressing sample (GnT-V-treated) and in the control. As a result, as shown in FIG. 2, the expression level of the total marker glycoprotein was not much different between the two groups; the GnT-V overexpressing group (GnT-V-treated) and the control. That is, the total expression level of the marker glycoprotein represented by the marker peptide having the peptide mass of 1685.8 among the marker peptides (see Table 1) was not affected significantly by GnT-V over-expression (without separation using lectin, see FIG. 2). In the meantime, the expression level of glycan-isoform having a specific glycan chain structure was significantly affected by GnT-V overexpression (with separation using lectin, see FIG. 1).

Therefore in this invention, mass spectrometry was performed only with the marker glycoprotein isoform having a specific glycan chain structure showing quantitative changes sensitively by N-acetylglucosaminyltransferase, the glycosyltransferase overexpressed in many types of cancer cells, indicating that the marker of the invention can be effectively used for the distinguishment of cancer patient group from normal group. Selective separation of the glycan-isoform having a specific glycan chain structure from all different kinds of glycan-isoforms of marker glycoproteins can be achieved by using proper lectin. Quantitative analysis of the glycan-isoform having a specific glycan chain structure can be performed by analyzing the hydrolyzed marker peptide derived from the marker glycoprotein. Theoretically, all the peptides hydrolyzed during the hydrolysis of the marker glycoprotein can be used as marker peptides. The screened marker peptides can be used as the marker peptides for diagnosis, prognosis, or verification of cancer by using human blood samples. In addition, the present inventors confirmed that quantitative analysis performed with a combination of one or more marker peptides can give more reliable results.

In a preferred embodiment of the present invention, clinical blood samples were used to investigate if the colon cancer patient group could be distinguished from the normal healthy group by using the marker peptide represented by SEQ. ID. NO: 3 (peptide mass, 1685.8). Particularly, pooled cancer plasma was prepared by mixing blood samples obtained from 10 patients clinically diagnosed as colon cancer. In the meantime, pooled control plasma was also prepared by mixing blood samples obtained from 10 normal healthy people clinically confirmed not to have any cancer related disease. Lectin selective protein samples were separated from both blood samples of the cancer patient group and the normal control group, followed by hydrolysis to prepare peptide samples of the cancer patient group and the normal control group. The target marker peptides were concentrated from the peptide samples by using the anti-peptide antibody, and then LC/MRM was repeatedly performed with the marker peptide (peptide mass, 1685.8) represented by SEQ. ID. NO: 3. As a result, as shown in Table 3, FIG. 4, and FIG. 5, approximately 2.4 fmol of the marker peptide was quantified only in the colon cancer group. The marker peptide was not detected or quantified in the normal control group (see Table 3, FIG. 4, and FIG. 5).

Therefore, it was confirmed that the marker peptide (peptide mass: 1685.8) screened and confirmed by using lectin in this invention showed high specificity to colon cancer In conclusion, the marker peptides screened in this invention can be effectively used for the distinguishment of colon cancer patient from normal healthy people by analyzing blood samples. In addition, the reliability of the marker glycoprotein of the present invention can be much increased by using a combination of one or more marker peptides simultaneously generated by hydrolysis of a single marker glycoprotein for quantitative analysis.

The present invention also provides a kit for diagnosing cancer comprising an antibody or a combination of antibodies specifically binding to one or more marker peptides selected from the group consisting of the marker peptides of the present invention.

The present invention also provides a use of the antibody or the combination of antibodies specifically binding to one or more marker peptides selected from the group consisting of the marker peptides of the present invention for the preparation of the kit for diagnosing cancer.

In this invention, the marker peptide is preferably the polypeptide having one of the amino acid sequences each represented by SEQ. ID. NO: 1-NO: 6, but not always limited thereto.

In this invention, the marker peptide is the one selected from the group consisting of the peptides each having the molecular weight of 2294.1, 2015.0, 1685.8, 1346.7, 1265.7 and 1109.5, but not always limited thereto.

In this invention, the cancer is preferably the one selected from the group consisting of colon cancer, liver cancer, stomach cancer, lung cancer, uterine cancer, breast cancer, prostatic cancer, thyroid cancer, and pancreatic cancer, but not always limited thereto.

In this invention, the said kit facilitates monitoring, diagnosing, or screening of cancer by detecting quantitative changes in marker peptides generated by treating a sample obtained from a subject with a hydrolase.

In this invention, the said kit can additionally include the marker peptides or their isotope-labeled peptides as standard materials.

In this invention, the antibody usable in the kit includes polyclonal antibody, monoclonal antibody, and epitope linkable fragment, etc. The polyclonal antibody can be produced by the conventional method comprising the steps of injecting one of the peptide markers to an animal; drawing blood from an animal; and obtaining serum containing the antibody. Such polyclonal antibody can be produced using a host animal selected from the group consisting of goat, rabbit, sheep, monkey, horse, pig, cow, dog, etc, and purified by the conventional method well-known to those in the art. The monoclonal antibody can be prepared by any technique that can provide antibody molecules through continuous culture of cell line, which is exemplified by hybridoma technique, human B-cell hybridoma technique, and EBV-hybridoma technique (Kohler G et al., *Nature* 256:495-497, 1975; Kozbor D et al., *J Immunol Methods* 81:31-42, 1985; Cote R J et al., *Proc Natl Acad Sci* 80:2026-2030, 1983; and Cole S P et al., *Mol Cell Biol* 62:109-120, 1984), but not always limited thereto. Also, the antibody fragment containing the specific binding site to one of those peptide markers can be prepared (Huse W D et al., *Science* 254: 1275-1281, 1989). The method to prepare such peptide specific antibody having specific sequence is well known to those in the art.

In this invention, the antibody used in the kit of the present invention can be fixed on a solid substrate to make post-steps such as washing or isolation easy. The solid substrate herein is exemplified by synthetic resin, nitrocellulose, glass board, metal board, glass fiber, microsphere, and microbead, but not always limited thereto. The synthetic resin herein is exemplified by polyester, polyvinyl chloride, polystyrene, polypropylene, PVDF, and nylon, but not always limited thereto.

In this invention, the sample obtained from a subject is contacted with the antibody binding specifically to one of the peptide markers fixed on the solid substrate. At this time, the sample can be diluted properly before the contact.

In this invention, after contacting the sample obtained from a subject with the antibody binding specifically to one of the peptide markers fixed on the solid substrate, unbound proteins are removed by washing, followed by detection of the marker peptides.

In this invention, the kit of the present invention can additionally include an antibody for detection binding specifically to the said peptide marker. The antibody for detection herein can be a conjugate labeled with coloring enzyme, fluorescent material, radio-isotope, or colloid, etc, and preferably a secondary antibody binding specifically to the said marker, but not always thereto. The coloring enzyme herein can be peroxidase, alkaline phosphatase, or acid phosphatase (ex: horseradish peroxidase), but not always limited thereto. The fluorescent material herein can be fluorescein carboxylic acid (FCA), fluorescein isothiocyanate (FITC), fluorescein thiourea (FTH), 7-acetoxycourmarin-3-yl, fluorescein-5-yl, fluorescein-6-yl, 2',7'-dichlorofluorescein-5-yl, 2',7'-dichlorofluorescein-6-yl, dihydrotetramethylrhosamine-4-yl, tetramethylrhodamine-5-yl, tetramethylrhodamine-6-yl, 4,4-difluoro-5,7-dimethyl-4-bora-3a,4a-deaza-s-indacene-3-ethyl or 4,4-difluoro-5,7-diphenyl-4-bora-3a,4a-deaza-s-indacene-3-ethyl, but not always limited thereto.

In this invention, the said kit can additionally include a substrate to be reacted with coloring enzyme, and washing fluid or eluent to eliminate unbound proteins and to keep conjugated peptide markers only.

The present invention also provides a biochip for diagnosing cancer comprising a biomolecule specifically binding to one or more marker peptides selected from the group consisting of the marker peptides of the present invention is integrated on the solid substrate.

The present invention also provides a use of the biomolecule specifically binding to one or more marker peptides selected from the group consisting of the marker peptides of the present invention for the preparation of the biochip for diagnosing cancer.

In this invention, the marker peptide is preferably the polypeptide having one of the amino acid sequences each represented by SEQ. ID. NO: 1-NO: 6, but not always limited thereto.

In this invention, the marker peptide is preferably the one selected from the group consisting of the peptides each having the molecular weight of 2294.1, 2015.0, 1685.8, 1346.7, 1265.7 and 1109.5, but not always limited thereto.

In this invention, the cancer is preferably the one selected from the group consisting of colon cancer, liver cancer, stomach cancer, lung cancer, uterine cancer, breast cancer, prostatic cancer, thyroid cancer, and pancreatic cancer, but not always limited thereto.

In this invention, the said biochip facilitates monitoring, diagnosing, or screening of cancer by detecting quantitative changes in marker peptides generated by treating a sample obtained from a subject with a hydrolase.

In this invention, the biomolecule is preferably an antibody or an aptamer, but not always limited thereto. The said biomolecule indicates not only a small molecule such as primary metabolite, secondary metabolite and natural substance but also an organic molecule produced by living organism such as protein, polysaccharide and nucleic acid. The aptamer herein indicates oligonucleotide or peptide binding to the specific target molecule.

In this invention, the solid substrate is preferably selected from the group consisting of plastic, glass, metal, and silicon, but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Sample Preparation

To overexpress N-acetylglucosaminyltransferase (GnT-V), the glycosyltransferase overexpressed in cancer cells, human colon cancer cells were transfected with MGAT5, resulting in the preparation of stable transfectant cells. Then, the GTN-V overexpressing cells (GnT-V-treated cells) and the control cells were cultured. Equal amounts of culture fluids obtained from both group were concentrated until the volume reached 2 ml respectively. The concentrated samples were reduced using 14 mM β-mercaptoethanol, followed by desalting. One mg of the desalted protein was loaded to L-PHA-avidin-agarose beads, to which phosphate-buffered saline (PBS) was added. The mixture stood at 4° C. for 12 hours. The lectin conjugated protein was washed with PBS three times, and then the protein was separated from lectin by using 6 M urea. The obtained protein was 10-fold diluted with 50 mM ammonium bicarbonate, followed by hydrolysis using 10 ug of trypsin for overnight at 37° C. with 1 mM $CaCl_2$. The hydrolyzed peptide was dried under reduced pressure to give 100 ul liquid. For the sample that had not been through lectin separation, 100 ug of each protein obtained from reduction and desaltation of the concentrated culture fluid was hydrolyzed. The hydrolyzed peptide was dried under reduced pressure to give 100 ul liquid.

Example 2

Selection of Marker Candidates Via Peptide Analysis

HPLC (high-performance liquid chromatography) was performed using trap column (C18, 5 um, 300×5 mm) and analytical column (C18, 5 um, 75 um×10 cm) to analyze the samples prepared in Example 1, followed by LC/ESI-MS/MS using LTQ-FT mass spectrometer (Thermo Finnigan), the electrospray ionization (ESI) mass spectrometer. Each sample protein was hydrolyzed by using trypsin to obtain peptides. Some of the prepared peptide samples were 10-fold diluted, which proceeded to liquid chromatography connected to the mass spectrometer by 10 µl.

Based on the results of the mass spectrometry, various proteins were qualified from the samples obtained from the GnT-V treated cell line and the normal control cell line by using search engines such as MASCOT and SEQUEST. The relative amount of each protein existed in each sample was calculated based on the frequency of qualitative analysis of each protein. Significant proteins were screened from the peptides obtained by LC/ESI-MS/MS and their analysis frequencies. Glycosylation of the screened protein and relevancy of the protein with cancer were investigated by using protein database including NCBInr DB, etc, related papers and descriptions, etc. As a result, candidate glycoproteins implying high chance of relevancy with cancer were selected. It was investigated whether or not the selected glycoprotein candidates could be used as cancer markers by quantitative analysis using multiple reaction monitoring mass spectrometry (MRM MS) with the peptides obtained by hydrolyzing the protein.

Among the marker peptides (Table 1) generated by hydrolysis of the cell membrane glycoprotein (MW: 159 kDa, Theoretical pI: 5.61) believed as a promising cancer marker, the present inventors have confirmed the possibility of using the peptide having the peptide mass of 1346.7 as a marker by MRM MS.

TABLE 1

| Peptide Number | Peptide Mass | Peptide Sequence | SEQ. ID. NO |
|---|---|---|---|
| 1 | 2294.1 | EPLDPNGIITQYEISYSSIR | SEQ. ID. NO: 1 |
| 2 | 2015.0 | GAPISAYQIVVEELHPHR | SEQ. ID. NO: 2 |
| 3 | 1685.8 | LWHLDPDTEYEIR | SEQ. ID. NO: 3 |
| 4 | 1346.7 | GSGVSNFAQLIVR | SEQ. ID. NO: 4 |
| 5 | 1265.7 | GLNPGTLNILVR | SEQ. ID. NO: 5 |
| 6 | 1109.5 | SLQGTSFENK | SEQ. ID. NO: 6 |

The marker peptides shown in Table 1 were all generated from one glycoprotein by hydrolysis, so that all the peptides of Table 1 can be used as a representative of the glycoprotein in mass spectrometry.

Example 3

Confirmation of Marker Glycoprotein by Mass Spectrometry

10 µl of each peptide sample prepared from the protein of each subject in Example 1 was taken, to which 50 fmol of the marker peptide standard material was added to make the total volume 50 µl. 4 samples were prepared; 2 of them were through lectin separation and the other 2 were not finished with lectin separation. The standard material labeled with target peptide isotope was the synthetic standard material that had the identical amino acid sequence with the target peptide (marker peptide) but was different in peptide mass. This material was used as an internal standard material in MRM MS. In quantitative mass spectrometry, calibration curve was made according to the changes of concentrations of the target peptide and the synthetic standard material under the same analysis conditions.

A part (10 μl) of each prepared sample (50 μl) was used for LC/MRM MS. Quantitative analysis was performed in triplicate with the marker peptide (peptide mass, 1346.7) by MRM MS and the results are shown in Table 2.

TABLE 2

|  | Sample | av · (fmol) | RSD (%) |
|---|---|---|---|
| With lectin separation | Control | 0.16 | 7.3 |
|  | GnT-V treated | 3.17 | 5.7 |
| Without lectin separation | Control | 4.19 | 6.2 |
|  | GnT-V treated | 3.57 | 1.9 |

As shown in Table 2, the results obtained from the triplicated quantitative analysis with each sample demonstrated very satisfactory relative standard deviations. These results indicate that the quantitative analysis for the marker peptide of the present invention is very stable and thus the marker peptide is highly reliable. Even at the hundreds of attomol level, the marker peptide can be quantified with low standard deviation but with high sensitivity. In particular, when comparing two samples obtained by performing lectin separation (GnT-V treated group and control group), detected amount of the marker peptide in the GnT-V treated group was 19.9 fold higher (FIG. 1) than that of the control group. However, difference of the marker peptide amount in the two samples obtained by not-performing lectin separation was not that much (0.9 fold, FIG. 2). The above results indicate that the marker peptide screened and confirmed by using lectin (peptide mass, 1346.7) has high specificity against cancer cells overexpressing GnT-V. In addition, liability to the marker glycoprotein of the present invention can be increased by using a combination of one or more marker peptides listed in Table 1 for quantitative mass spectrometry.

Example 4

Confirmation of Marker Glycoprotein by Using Clinical Blood Sample

Pooled cancer plasma was prepared by mixing blood samples obtained from 10 patients clinically diagnosed as colon cancer. Pooled control plasma was also prepared by mixing blood samples obtained from 10 healthy people who were clinically confirmed not to have any kind of cancer. Lectin selective protein samples were separated from both blood samples of the cancer patient group and the control group by the same manner as described in Example 1, followed by hydrolysis to prepare peptide samples of the cancer patient group and the control group. For a supporter for the fixation of lectin, various supporters including magnetic beads, in addition to agarose beads of Example 1, can be used. In this invention, streptavidine-magnetic beads were used for the fixation of lectin. Particularly, blood samples of the colon cancer patient group and the normal control group were added to L-PHA-streptavidine-magnetic beads in phosphate-buffered saline (PBS), which stood at 4° C. for 12 hours. Lectin conjugated proteins were washed with PBS three times, and then the proteins bound to lectin were eliminated by using 2 M urea/DDT solution. The obtained proteins were treated with iodoacetamide (IAA), and then 2-fold diluted with 50 mM ammonium bicarbonate. Hydrolysis was performed by using trypsin at 37° C. for overnight. The hydrolyzed peptides were dried under reduced pressure.

The standard material labeled with isotope of the marker peptide (peptide mass, 1685.8) represented by SEQ. ID. NO: 3 (Table 1) was added to each sample equally, and used as an internal control material for quantitative analysis.

The target protein exists in blood at a very low concentration, so that the target marker peptide cannot be detected from the prepared peptide sample by MRM right away. Therefore, the target marker peptide was concentrated from each of the prepared peptide sample by using the target marker peptide (SEQ. ID. NO: 3) selective peptide antibody (anti-peptide antibody). At this time, the anti-peptide antibody can be fixed directly on polymer solid or magnetic solid for the convenience of experiment, or fixed indirectly by using avidine-biotin linker, etc. In this invention, the anti-peptide antibody was directly fixed on magnetic beads.

Figure 4:
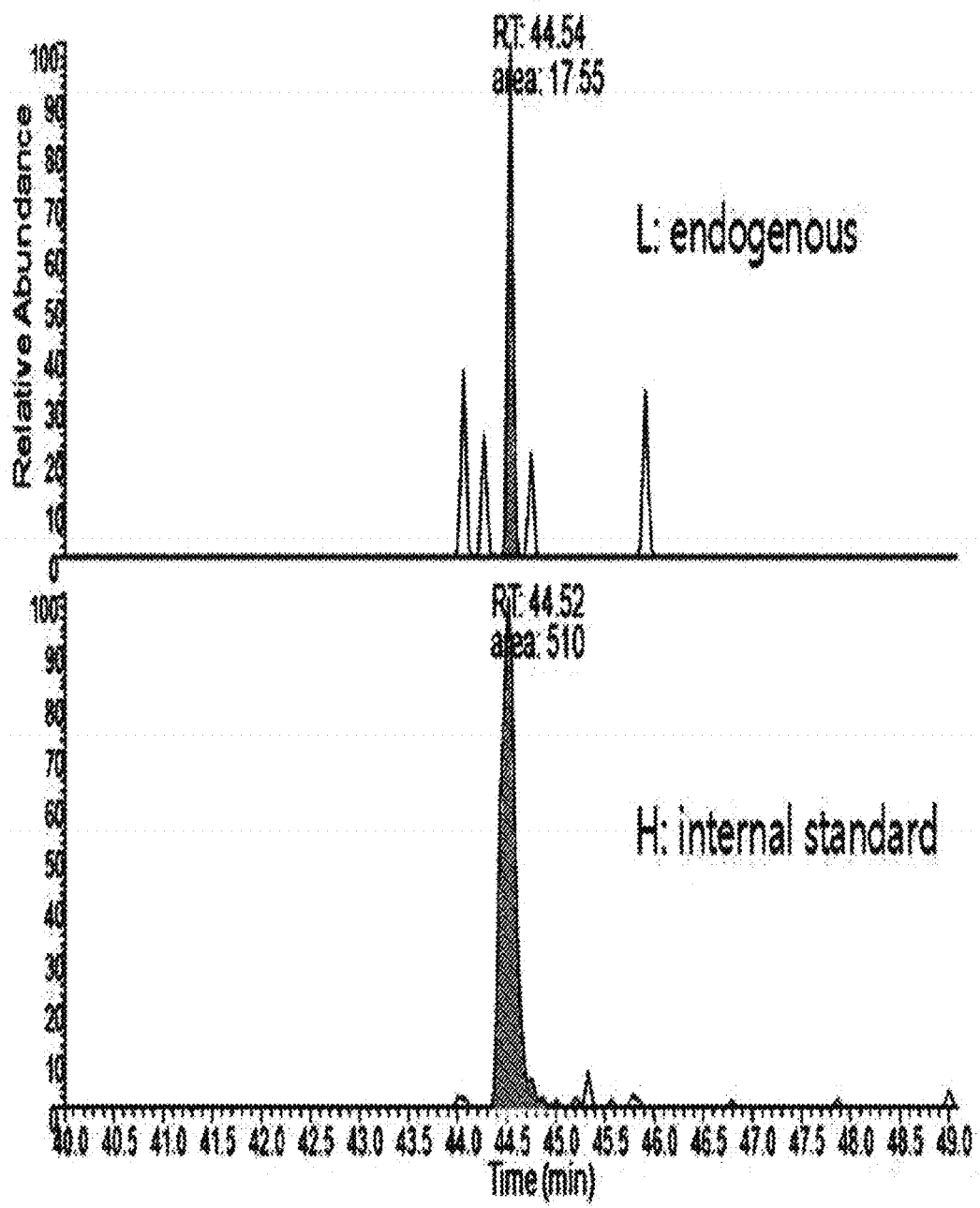
FIG. 4 is a diagram showing the chromatogram illustrating the transition of the marker peptide represented by SEQ. ID. NO: 3 obtained by LC/MRM with the blood sample of the colon cancer patient group.
Figure 5:
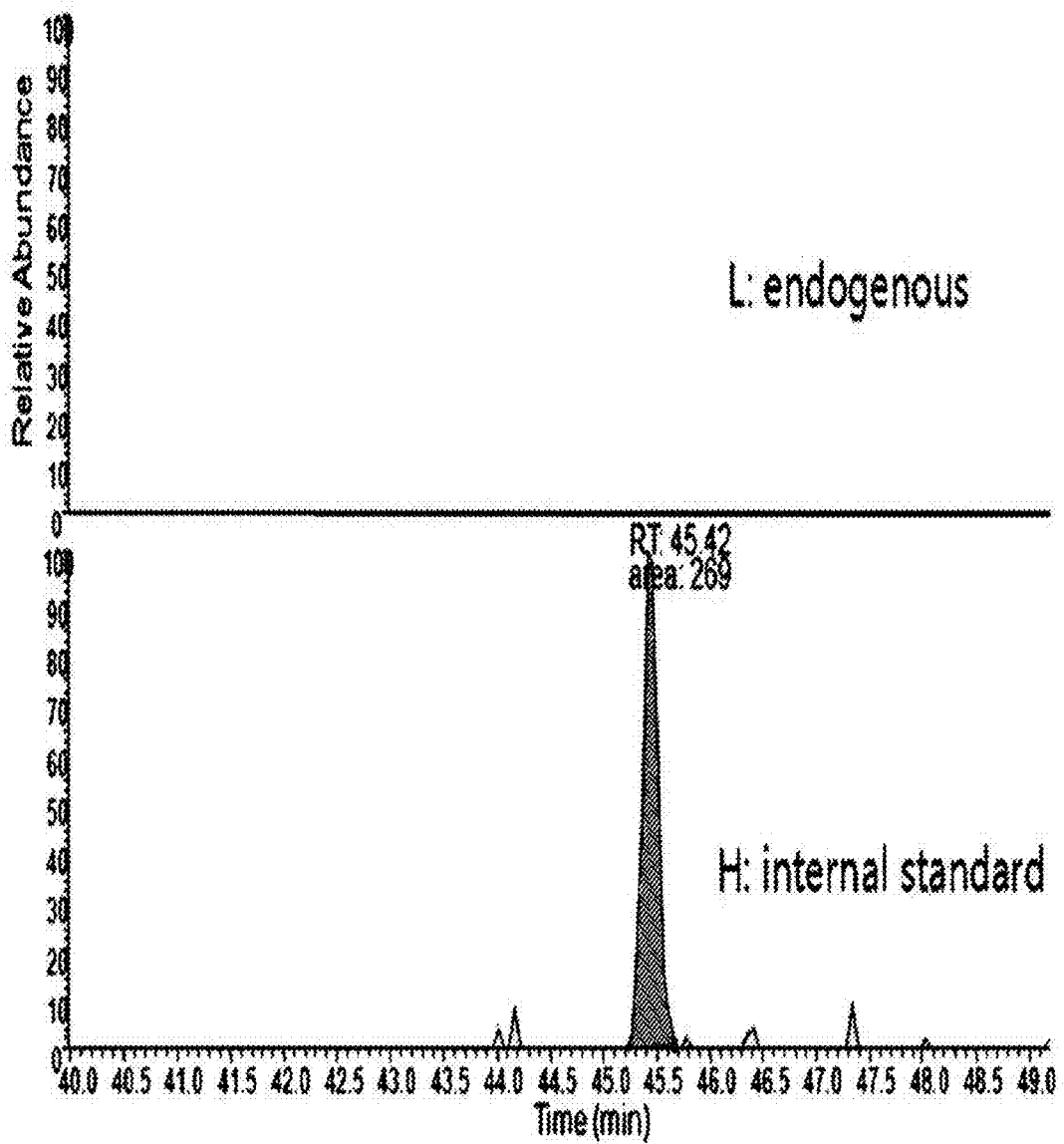
FIG. 5 is a diagram showing the chromatogram illustrating the transition of the marker peptide represented by SEQ. ID. NO: 3 obtained by LC/MRM with the blood sample of the normal control group. Herein, the endogenous marker peptide was not detected.

The glycoprotein sample concentrated by lectin was hydrolyzed. Then, the marker peptide was concentrated from the hydrolyzed peptide sample by using the anti-peptide antibody, followed by LC/MRM. FIG. 4 is an example of chromatogram illustrating the transition of the marker peptide (SEQ. ID. NO: 3) obtained by LC/MRM with the colon cancer group sample. FIG. 5 is an example of chromatogram illustrating the transition of the marker peptide (SEQ. ID. NO: 3) obtained by LC/MRM with the normal control group sample. The endogenous marker peptide and the internal standard were simultaneously eluted on chromatography in the colon cancer group (FIG. 4). In the meantime, the endogenous marker peptide was not detected in the normal control group (FIG. 5). The quantitative analysis was repeated. As a result, as shown in Table 3, the marker peptide was quantified at the level of 2.4 fmol in the colon cancer group, while the marker peptide was not detected or quantified in the normal control group.

TABLE 3

| Sample | Blood Sample (ul) | Internal Control (fmol) | MRM Quantitative Value (av · fmol) | Marker Peptide Conc. (av · ng/ml) |
|---|---|---|---|---|
| Colon Cancer Group | 30 | 100 | 2.361 | 0.1 |
| Normal Control Group | 30 | 100 | Not Detected | Not Detected |

The above results indicate that the marker peptide represented by SEQ. ID. NO: 3 (peptide mass, 1685.8) screened and confirmed by using lectin hereinabove has high specificity to colon cancer.

Therefore, it was confirmed that the marker peptide of the present invention can be effectively used for the distinguishment of the colon cancer patient group from the normal healthy group by analyzing blood samples. In addition, the reliability of the marker peptide of the present invention can be much increased by using a combination of one or more marker peptides listed in Table 1 which are simultaneously generated by hydrolysis of a single marker glycoprotein.

INDUSTRIAL APPLICABILITY

As explained hereinbefore, the present invention provides a method for screening a cancer marker, a method for confirming the same, and a method for diagnosing cancer using the said marker peptide.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for diagnosing colon cancer, comprising:
   1) contacting a human blood sample obtained from a subject with lectin to separate glycoproteins from the human blood sample;
   2) hydrolyzing the glycoproteins to obtain polypeptides;
   3) concentrating the polypeptides by using a polypeptide-selective antibody;
   4) analyzing the concentrated polypeptides by mass spectrometry; and
   5) diagnosing colon cancer or high risk of colon cancer when the subject-has at least one polypeptide selected from the group consisting of these polypeptides having the molecular weights of 2294.1, 2015.0, 1685.8, 1346.7, 1265.7 and 1109.5 confirmed by the analysis of step 4).

2. A method for diagnosing colon cancer comprising:
   1) contacting a human blood sample obtained from a subject with lectin to separate glycoproteins from the human blood sample;
   2) hydrolyzing the glycoproteins to obtain polypeptides;
   3) sequencing and quantitatively analyzing the polypeptides by mass spectrometry; and
   4) diagnosing cancer or high risk of cancer when the sequencing and quantitative analysis of step 3) identifies at least one polypeptide is selected from the group consisting of those polypeptides having the amino acid sequences represented by SEQ. ID. NO: 1-SEQ ID NO: 6 and selected from the group consisting of those polypeptides having the molecular weights of 2294.1, 2015.0, 1685.8, 1346.7, 1265.7 and 1109.5.

3. The method according to claim 1, wherein the lectin of step 1) is the one or a combination of at least two of those characteristically selected from the group consisting of ConA (Concanavalin A), WGA (wheat germ agglutinin), Jacalin, SNA (*Sambucus Nigra*), AAL (*Aleuria aurantia* agglutinin), L-PHA (L-phyto agglutinin), PNA (peanut agglutinin), LCA (lens culinaris agglutinin), ABA (Agaricus bisporus agglutinin), DBA (Dolichos biflorus agglutinin), DSA (Datura stramonium agglutinin), ECA (Erythrina cristagalli agglutinin), SBA (soybean agglutinin), SSA (Sambucus sieboldiana agglutinin), UEA (Ulex europaeus agglutinin), VVL (Vicia villosa lectin), and BPL (Bauhinia purpurea lectin).

4. The method according to claim 1, wherein the hydrolysis of step 2) is performed by using one of enzymes characteristically selected from the group consisting of Arg-C, Asp-N, Glu-C, Lys-C, chymotrypsin, and trypsin.

5. The method according to claim 2, wherein the hydrolysis of step 2) is performed by using one of enzymes characteristically selected from the group consisting of Arg-C, Asp-N, Glu-C, Lys-C, chymotrypsin, and trypsin.

* * * * *